United States Patent
Bernard et al.

(10) Patent No.: US 6,569,110 B2
(45) Date of Patent: May 27, 2003

(54) SPLINT FOR SURGERY OF LACRIMAL PASSAGES

(75) Inventors: Jean-Antoine Bernard, Paris (FR); Patrick Klap, Paris (FR)

(73) Assignee: France Chirurgie Instrumentation, F.C.I., Les Moulineaux (FR)

( * ) Notice: Subject to any disclaimer, the term of this patent is extended or adjusted under 35 U.S.C. 154(b) by 0 days.

(21) Appl. No.: 09/950,553

(22) Filed: Sep. 11, 2001

(65) Prior Publication Data

US 2002/0077573 A1 Jun. 20, 2002

(30) Foreign Application Priority Data

Sep. 12, 2000 (FR) .............................. 00 11568

(51) Int. Cl.[7] .................................. A61F 5/00
(52) U.S. Cl. .......................... 602/5; 600/199
(58) Field of Search ................ 602/5, 6; 128/846, 128/848, 858; 600/199, 204.45

(56) References Cited

U.S. PATENT DOCUMENTS

| 2,757,665 A | * | 8/1956 | Tanikawa | |
| 3,935,859 A | * | 2/1976 | Doyle | 128/89 R |
| 4,921,485 A | | 5/1990 | Griffiths | |
| 5,062,831 A | | 11/1991 | Griffiths | |
| 5,094,233 A | * | 3/1992 | Brennan | 602/6 |
| 5,601,594 A | * | 2/1997 | Best | 606/199 |
| 6,015,425 A | * | 1/2000 | Altadonna | 606/204.45 |

FOREIGN PATENT DOCUMENTS

| EP | 0387155 | 9/1990 |
| SU | 1009461 | 4/1983 |
| SU | 1803079 | 3/1993 |
| WO | 99/65544 | 12/1999 |

* cited by examiner

Primary Examiner—Michael A. Brown
(74) Attorney, Agent, or Firm—Greenblum & Bernstein, P.L.C.

(57) ABSTRACT

Splint for surgery of lacrimal passages includes a plate adapted for insertion in a nasal passage, the plate comprising two arms made of a flexible material, the two arms defining therebetween an open angle, a convex side being formed on the plate opposite the open angle and a flange formed on a first edge of one of the arms, the flange being located on the convex side of the plate.

12 Claims, 1 Drawing Sheet

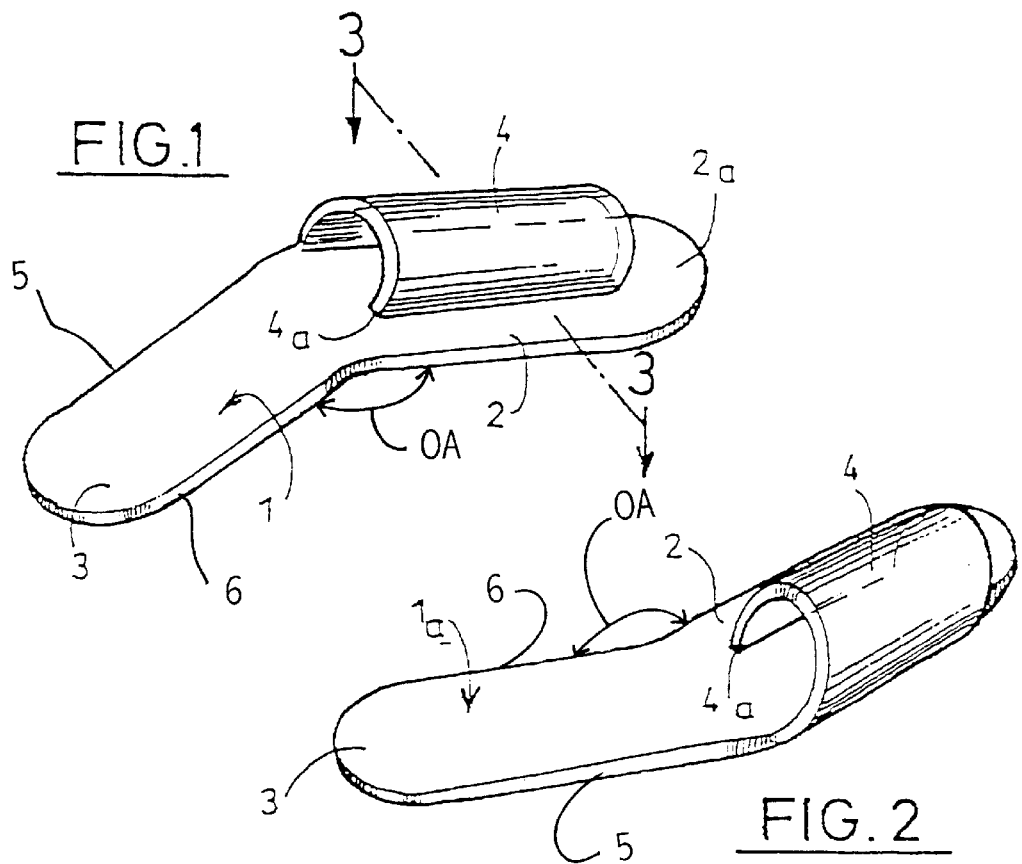
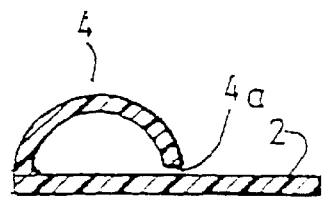

SPLINT FOR SURGERY OF LACRIMAL PASSAGES

CROSS-REFERENCE TO RELATED APPLICATIONS

The present application claims priority under 35 U.S.C. §119 of French Patent Application No. 00/11568, filed Sep. 12, 2000.

BACKGROUND OF THE INVENTION

1. Field of the Invention

The present invention relates to a splint for surgery of the lacrimal passages.

2. Discussion of Background Information

The invention relates to a splint which can be used more particularly for endonasal dacryocystorhinostomy, an operation which consists of anastomosing the lacrimal sac in the nasal cavities, following an obstruction of the lacrimal passages.

After performing such an operation, tents are inserted into the nasal cavity for hemostasis. These tents are uncomfortable for the patient, and often constitute a source of infection.

SUMMARY OF THE INVENTION

One of the objects of the present invention is to obtain a splint that is easy to manufacture, easy to use for the surgeon, and which ensures proper healing under improved conditions of comfort for the patient: nasal breathing preserved, absence of postoperative infections and foul smells.

The splint according to the invention is characterized in that it is constituted of a small plate made of a flexible material forming two arms arranged along an open angle, one of the arms having, along its edge located on the outer side, a flange that projects on one of its surfaces.

Of course, a splint corresponding to the left side and one corresponding to the right side are provided.

After the operation, the splint is engaged into the nasal cavity such that the flange is opposite the lacrimal sac, the flange being open at its ends. This enables the patient to breathe freely, which is more comfortable than the commonly used tents, which tents often constitute a source of postoperative infections and foul smells.

Preferably, the flange is slightly elastic.

According to a constructional detail, the flange has the shape of a cylindrical ungula.

Finally, according to a last characteristic, the edge of the flange, opposite that affixed to the edge of the corresponding arm is free, a small space being provided between the free edge and the corresponding surface of the arm.

According to an aspect of the invention, a splint for surgery of lacrimal passages includes a plate adapted for insertion in a nasal passage, the plate comprising two arms made of a flexible material, the two arms defining therebetween an open angle, an outer side being formed on the plate opposite the open angle and a flange formed on a first edge of one of the arms, the flange being located on the outer side of the plate.

The flange may project upwardly from a plane of the one of the arms. The flange may be elastic. The flange may have the shape of an ungula of a cylinder. The splint may further comprise a second edge on the one of the arms of the flange, the second edge being free and being located opposite the first edge, and may further comprise a small space between the second edge and a corresponding surface of the one of the arms.

According to a further aspect of the invention, a splint for surgery of lacrimal passages includes a plate adapted for insertion in a nasal passage, the plate comprising two arms made of a flexible material. The two arms define therebetween an open angle. An open side is formed on the plate opposite the open angle. An elastic flange is formed on a first edge of one of the arms, the flange being located on the open side of the plate, projecting upwardly from a plane of the one of the arms and having the shape of an ungula of a cylinder. A second edge is formed on the one of the arms of the flange, the second edge being free and being located opposite the first edge. A small space is formed between the second edge and a corresponding surface of the one of the arms.

The present invention is further described in the detailed description which follows, in reference to the noted plurality of drawings by way of non-limiting exemplary embodiments of the present invention, in which like reference numerals represent similar parts throughout the several views of the drawings, and wherein:

BRIEF DESCRIPTION OF THE DRAWINGS

FIG. 1 and FIG. 2 are perspective views of a splint according to the invention, one being adapted to the left nasal cavity and the other to the right nasal cavity.

FIG. 3 is a cross-sectional view along the line 3—3 of FIG. 1.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

The splint shown in FIGS. 1 and 2 is constituted of a small plate 1 made of a flexible material having two arms 2 and 3 forming an open angle OA between the inner sides 6 of the respective arms 2 and 3, whose ends are slightly rounded.

The arm 2, along its edge 2a and on the outer side 5 of the small plate 1, is affixed to a slightly elastic flange 4, the latter having the general shape of a cylindrical ungula whose both planes demarcating the ungula are located in the same plane.

The edge 4a of the flange 4 opposite that affixed to the edge 2a is free and is in normal position, located a few millimeters from the surface of the arm 2.

The splint of FIG. 1 is adapted to be used on the left side. FIG. 2 shows a splint 1a adapted to the right side, the latter being obtained in the same manner as that which described in FIG. 1.

After an operation adapted to treat an obstruction of the lacrimal passages, as a result of dacryocystitis, for example, the splint according to the invention is inserted into the nasal cavity, such that the flange 4 is opposite the lacrimal sac. The latter, due to its elasticity, makes it possible to hold the walls of the nasal cavity apart, thereby allowing the free passage of tears. In addition, the patient can breathe freely, which is more comfortable.

To prevent the splint, which can be kept for several days, from moving, it can be fixed by one or more threads running through the small plate and the nasal septum.

Of course, the invention is not limited to the embodiment that has just been described and shown. Numerous detailed modifications can be made thereto without departing from the scope of the invention.

LIST OF REFERENCE CHARACTERS 1, 1a small plate
2 arm
2a edge
3 arm
4 elastic flange
4a edge
5 outer angled side
6 inner angled side
OA open angle

What is claimed is:

1. Splint for surgery of lacrimal passages, including a plate adapted for insertion in a nasal passage, said plate comprising:

two arms made of a flexible material;

said two arms being oriented at an angle with respect to each other;

an outer angled side formed on said plate opposite an inner angled side; and a flange attached to an edge of one of the arms, said flange being attached to the outer angle side of said plate.

2. The splint according to claim 1, wherein said flange projects upwardly from a plane of said one of the arms.

3. The splint according to claim 2, wherein said flange is elastic.

4. The splint according to claim 3, wherein said flange has the shape of an ungula of a cylinder.

5. The splint according to claim 3, further comprising a second edge formed on an end of the flange, said second edge being free and being located opposite said edge on one of the arms, and further comprising a small space between said second edge and a corresponding surface of said one of the arms.

6. The splint according to claim 2, wherein said flange has the shape of an ungula of a cylinder.

7. The splint according to claim 6, further comprising a second edge formed on an end of the flange, said second edge being free and being located opposite said edge one of the arms, and further comprising a small space between said second edge and a corresponding surface of said one of the arms.

8. The splint according to claim 2, further comprising a second edge formed on an end of the flange, said second edge being free and being located opposite said edge on one of the arms, and further comprising a small space between said second edge and a corresponding surface of said one of the arms.

9. The splint according to claim 1, wherein said flange is elastic.

10. The splint according to claim 1, wherein said flange has the shape of an ungula of a cylinder.

11. The splint according to claim 1, further comprising a second edge formed on an end of the flange, said second edge being free and being located opposite said edge on one of the arms, and further comprising a small space between said second edge and a corresponding surface of said one of the arms.

12. Splint for surgery of lacrimal passages, including a plate adapted for insertion in a nasal passage, said plate comprising:

two arms made of a flexible material;

said two arms being oriented at an angle with respect to each other;

an outer angled side formed on said plate opposite an inner angled side;

an elastic flange attached to an edge of one of the arms, said flange being attached to an outer side of said plate, projecting upwardly from a plane of said one of the arms and having the shape of an ungula of a cylinder; and a second edge on said one of the arms of the flange, said second edge being free and being located opposite said first edge, and further comprising a small space between said second edge and a corresponding surface of said one of the arms.

* * * * *